(12) United States Patent
Jun

(10) Patent No.: US 10,088,447 B2
(45) Date of Patent: Oct. 2, 2018

(54) BIOSENSOR

(71) Applicant: Seung Ik Jun, San Jose, CA (US)

(72) Inventor: Seung Ik Jun, San Jose, CA (US)

( * ) Notice: Subject to any disclaimer, the term of this patent is extended or adjusted under 35 U.S.C. 154(b) by 0 days.

(21) Appl. No.: 15/283,106

(22) Filed: Sep. 30, 2016

(65) Prior Publication Data

US 2018/0095052 A1    Apr. 5, 2018

(51) Int. Cl.
| | |
|---|---|
| *G01N 27/41* | (2006.01) |
| *G01N 27/414* | (2006.01) |
| *H01L 29/417* | (2006.01) |
| *H01L 29/786* | (2006.01) |

(52) U.S. Cl.
CPC ... *G01N 27/4145* (2013.01); *H01L 29/41733* (2013.01); *H01L 29/786* (2013.01)

(58) Field of Classification Search
CPC ..................................................... G01N 27/00
See application file for complete search history.

(56) References Cited

U.S. PATENT DOCUMENTS

| | | | | |
|---|---|---|---|---|
| 2002/0106654 A1* | 8/2002 | Kojima | ................ | C12Q 1/6825 435/6.11 |
| 2005/0212016 A1* | 9/2005 | Brunner | ............ | B01L 3/502753 257/253 |
| 2007/0102304 A1* | 5/2007 | Tam | .................... | G01N 27/3271 205/792 |
| 2008/0205017 A1* | 8/2008 | Nellissen | .......... | B01L 3/502707 361/796 |
| 2009/0062146 A1* | 3/2009 | Takeuchi | ............. | B01J 19/0046 506/20 |
| 2009/0257917 A1* | 10/2009 | Nakamura | ......... | G01N 27/3271 422/68.1 |
| 2010/0320086 A1* | 12/2010 | Lee | .................... | G01N 33/5438 204/403.01 |
| 2011/0027816 A1* | 2/2011 | Fujiwara | ............ | G01N 27/3274 435/25 |
| 2012/0134880 A1* | 5/2012 | Kurkina | ............. | G01N 27/4146 422/82.01 |
| 2013/0028789 A1* | 1/2013 | Sakamoto | .......... | G01N 27/4145 422/82.01 |
| 2013/0243655 A1* | 9/2013 | Li | .......................... | G01N 33/50 422/82.05 |
| 2014/0017146 A1* | 1/2014 | Sakamoto | .......... | G01N 27/4145 422/430 |
| 2017/0097332 A1* | 4/2017 | Paik | ..................... | C12Q 1/6869 |

FOREIGN PATENT DOCUMENTS

KR    10-2008-0076434 A    8/2008

* cited by examiner

*Primary Examiner* — Caridad Everhart
*Assistant Examiner* — Ankush Singal

(57) ABSTRACT

Disclosed herein is a biosensor. The biosensor includes: a mount; a bio-sensing chip disposed on the mount and including at least one thin film transistor; a reaction layer disposed on the bio-sensing chip and including at least one of a biological sample and a biochemical reaction reagent; an upper electrode disposed on an upper surface of the reaction layer and supplying electric signal to the reaction layer; and at least one pad disposed on the bio-sensing chip and electrically connected to the bio-sensing chip. The biosensor can measure voltage-current characteristics in a linear region and a saturation region through examination with respect to a target substance using the thin film transistor.

17 Claims, 12 Drawing Sheets

BIOSENSOR

TECHNICAL FIELD

Exemplary embodiments of the present disclosure relate to a biosensor, and more particularly to a biosensor using electrical and electrochemical signals.

BACKGROUND

Measurement of concentrations of clinically important substances is an important issue in diagnosis and healthcare. Particularly, diagnosis and management of disease can be carried out based on measurement of target substances such as glucose, ketones, creatine, lactate, neutral fat, pyruvate, alcohol, bilirubin, NAD(P)H, uric acid, and the like in a biological sample such as blood.

In order to achieve accurate, rapid and economic measurement of the concentration of a clinically significant substance in the biological sample, an electrochemical biosensor is generally used in the art.

Such a conventional biosensor includes electrodes and a biochemical reaction reagent, and is configured to measure resistance variation corresponding to characteristics of current and voltage through electrochemical reaction. As a result, since the measurement result indicates a biochemical reaction result based on a gradient of resistance corresponding to the characteristics of current and voltage, the conventional biosensor has a problem of low reliability due to low measurement sensitivity and accuracy thereof.

One example of the background technique is disclosed in Korean Patent Laid-open Publication No. 10-2008-0076434 (2008.08.20).

SUMMARY

Exemplary embodiments of the present disclosure provide a biosensor that can improve measurement sensitivity and accuracy with respect to a target substance.

In accordance with one aspect of the present disclosure, a biosensor includes: a mount; a bio-sensing chip disposed on the mount and including at least one thin film transistor; a reaction layer disposed on the bio-sensing chip and including at least one of a biological sample and a biochemical reaction reagent; an upper electrode disposed on an upper surface of the reaction layer and supplying electric signal to the reaction layer; and at least one pad disposed on the bio-sensing chip and electrically connected to the bio-sensing chip.

The biosensor may further include a wall disposed on the bio-sensing chip to surround the reaction layer.

The at least one pad may include at least one of a readout pad, a gate driving pad, and a Vdd pad.

The bio-sensing chip may include a plurality of sub-cells regularly arranged and electrically connected to each other.

Each of the sub-cells may include a first thin film transistor contacting the reaction layer and detecting at least one of the biological sample and the biochemical reaction reagent on the reaction layer.

Each of the sub-cells may further include a second thin film transistor electrically connected to the first thin film transistor and reading out an electrochemical signal output from the first thin film transistor.

Each of the sub-cells may include a third thin film transistor contacting the reaction layer and detecting at least one of the biological sample and the biochemical reaction reagent on the reaction layer.

Each of the sub-cells may further include a fourth thin film transistor electrically connected to the third thin film transistor and reading out an electrochemical signal output from the third thin film transistor.

The biosensor may further include a sensing readout line and a Vdd line, wherein a gate electrode of the first thin film transistor may contact the reaction layer; a source electrode of the first thin film transistor may be electrically connected to the Vdd line; and a drain electrode of the first thin film transistor may be electrically connected to the sensing readout line.

The biosensor may further include a sensing readout line, a Vdd line and a gate line, wherein a gate electrode of the first thin film transistor may contact the reaction layer; a source electrode of the first thin film transistor may be electrically connected to the Vdd line; a drain electrode of the first thin film transistor may be electrically connected to a source electrode of the second thin film transistor; a drain electrode of the second thin film transistor may be electrically connected to the sensing readout line; and a gate electrode of the second thin film transistor may be electrically connected to the gate line.

The biosensor may further include a sensing readout line, a reference readout line and a Vdd line, wherein a gate electrode of the first thin film transistor may contact the reaction layer; a source electrode of the first thin film transistor may be electrically connected to the Vdd line; a drain electrode of the first thin film transistor may be electrically connected to the sensing readout line; a gate electrode of the third thin film transistor may contact the reaction layer; a source electrode of third thin film transistor may be electrically connected to the Vdd line; and a drain electrode of the third thin film transistor may be electrically connected to the reference readout line.

The biosensor may further include a sensing readout line, a reference readout line, a Vdd line and a gate line, wherein the gate electrode of the third thin film transistor may contact the reaction layer; a source electrode of third thin film transistor may be electrically connected to the Vdd line; a drain electrode of the third thin film transistor may be electrically connected to a source electrode of the fourth thin film transistor; a drain electrode of the fourth thin film transistor may be electrically connected to the reference readout line; and a gate electrode of the fourth thin film transistor may be electrically connected to the gate line.

Each of the sub-cells may include a gate surface disposed on the mount and provided at one side thereof with a first gate electrode; a first semiconductor active layer disposed on the first gate electrode; a first drain electrode disposed on the first semiconductor active layer and electrically connected to the first semiconductor active layer; and a first source electrode disposed on the first semiconductor active layer and electrically connected to the first semiconductor active layer while being electrically insulated from the first drain electrode.

The gate surface may contact the reaction layer.

One of the at least one pad may be a readout pad and the first drain electrode may be electrically connected to the readout pad.

One of the at least one pad may be a Vdd pad and the first source electrode may be electrically connected to the Vdd pad.

The biosensor may further include a gate line disposed on the mount and including a second gate electrode; and a second semiconductor active layer disposed on the second gate electrode.

The first drain electrode may be electrically connected at one side thereof to the first semiconductor active layer and at the other side thereof to the second semiconductor active layer.

Each of the sub-cells may include an analysis sensing region and a reference sensing region, and each of the analysis sensing region and the reference sensing region may include the gate surface, the first semiconductor active layer, the first drain electrode and the first source electrode.

The analysis sensing region may sense an electrochemical signal output from the reaction layer and the reference sensing region may measure a reference value for correcting the electrochemical signal sensed by the analysis sensing region.

BRIEF DESCRIPTION OF DRAWINGS

The accompanying drawings, which are included to provide a further understanding of the disclosed technology, and are incorporated in and constitute a part of this specification, illustrate exemplary embodiments of the disclosed technology, and together with the description serve to describe the principles of the disclosed technology.

DETAILED DESCRIPTION

Hereinafter, exemplary embodiments of the present disclosure will be described in detail with reference to the accompanying drawings.

Figure 1:
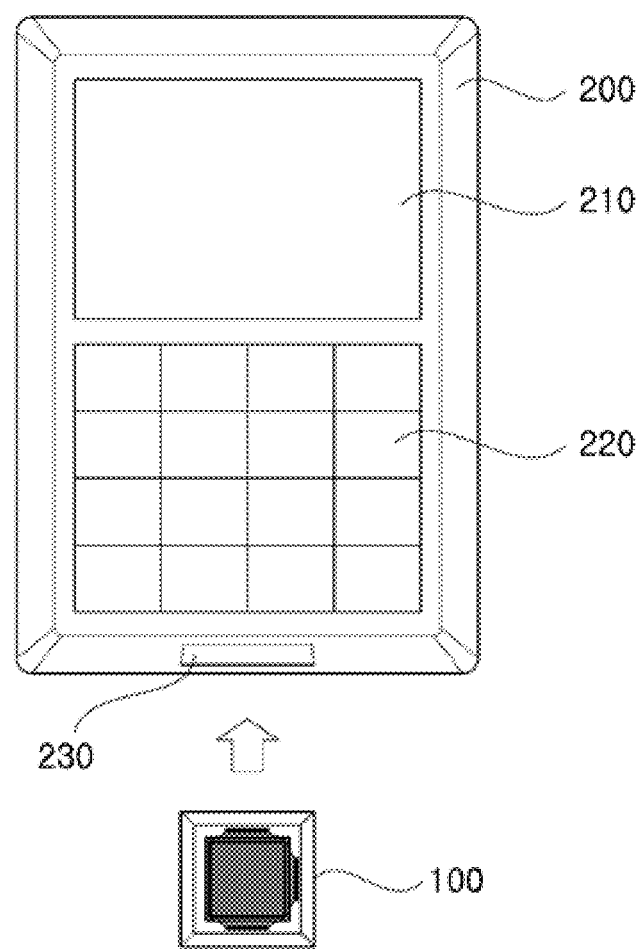
FIG. 1 is a plan view of a biosensor according to a first exemplary embodiment of the present disclosure and an analyzer.
Figure 2:
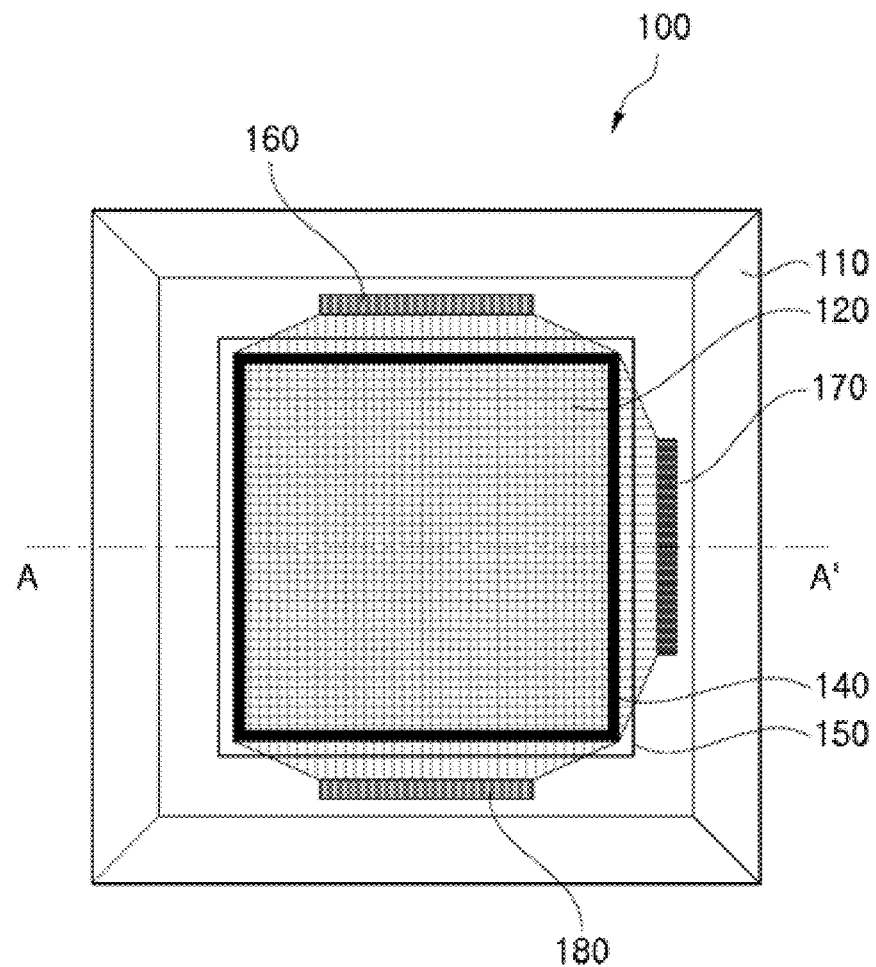
FIG. 2 is a plan view of the biosensor according to the first exemplary embodiment of the present disclosure.

FIG. 1 is a plan view of a biosensor according to a first exemplary embodiment of the present disclosure and an analyzer. FIG. 2 is a plan view of the biosensor according to the first exemplary embodiment of the present disclosure and FIG. 3 is a cross-sectional view taken along line A-A' of FIG. 2.

Figure 3:
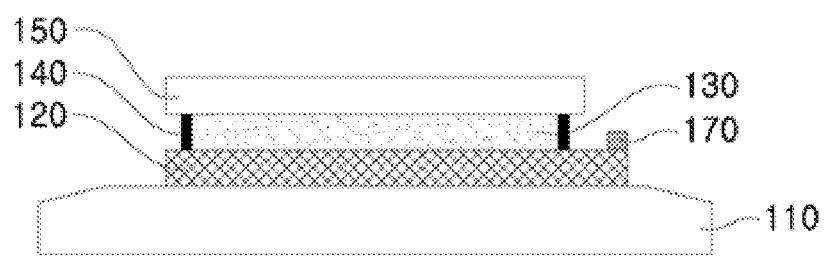
FIG. 3 is a cross-sectional view taken along line A-A' of FIG. 2.

Referring to FIG. 1 to FIG. 3, a biosensor 100 according to the first exemplary embodiment of the present disclosure includes a mount 110, a bio-sensing chip 120, a reaction layer 130, a wall 140, an upper electrode 150, a readout pad 160, a gate driving pad 170, and a Vdd pad 180.

The mount 110 supports the bio-sensing chip 120, the reaction layer 130, the wall 140, the upper electrode 150, the readout pad 160, the gate driving pad 170, and the Vdd pad 180. In this structure, with a biological sample and a reaction reagent included in the reaction layer 130, when the biosensor 100 is inserted into a biosensor insertion port 230 of an analyzer 200, electric signals such as voltage or current is supplied to the biosensor 100 and analysis is performed by the bio-sensing chip 120. Then, an analysis result is displayed on a display 210 of the analyzer 200. In addition, an input unit 220 may be disposed at a lower side of the display 210 of the analyzer 200 so as to be used by a user to input information for analysis.

The bio-sensing chip 120 processes electrochemical reactions generated in the reaction layer 130. The bio-sensing chip 120 is disposed on an upper surface of the mount 110 and the reaction layer 130 is disposed on an upper surface of the bio-sensing chip 120. The bio-sensing chip 120 may include a plurality of sub-cells 122, which will be described below.

The reaction layer 130 is disposed on the upper surface of the bio-sensing chip 120 and may include a biological sample and a biochemical reaction reagent. Here, the biological sample may be blood and the biochemical reaction reagent may also have a liquid phase. Thus, in order to prevent the biological sample and the biochemical reaction reagent included in the reaction layer 130 from flowing on the bio-sensing chip 120, the wall 140 may be disposed on the upper surface of the bio-sensing chip 120.

The wall 140 is disposed on the upper surface of the bio-sensing chip 120 such that a certain region can be formed inside the upper surface of the bio-sensing chip 120 along an edge of the bio-sensing chip 120. With this structure, the reaction layer 130 can be formed inside the wall 140 so as not to extend outside the bio-sensing chip 120.

The upper electrode 150 may be formed to cover upper surfaces of the reaction layer 130 and the wall 140. With this structure, the upper electrode 150 may act as a lid covering the reaction layer 130 and may supply electric signal from an external signal source to the reaction layer 130 such that the biological sample and the biochemical reaction reagent can react in the reaction layer 130. In this exemplary embodiment, the upper electrode 150 may have a monolayer structure or a stack structure formed of at least one of Pt, Au, Ag, Al, Al—Nd, Al—Cu, Mo, Ti, Ta, and Cr. Alternatively, the upper electrode 150 may have a monolayer structure or a stack structure formed of at least one of InSnO, SnO, InZnO and ZnO.

Each of the readout pad 160, the gate driving pad 170 and the Vdd pad 180 may be disposed on the bio-sensing chip 120 outside the wall 140. As shown in FIG. 2, the readout pad 160, the gate driving pad 170 and the Vdd pad 180 are disposed on three side surfaces of the bio-sensing chip 120, respectively, and may be electrically connected to the bio-sensing chip 120. Each of the readout pad 160, the gate driving pad 170 and the Vdd pad 180 may be electrically connected to a plurality of sub-cells 122 in the bio-sensing chip 120 to supply signal to each of the sub-cells 122 and to output an electrical signal with respect to data analyzed by each of the sub-cells 122.

Figure 4:
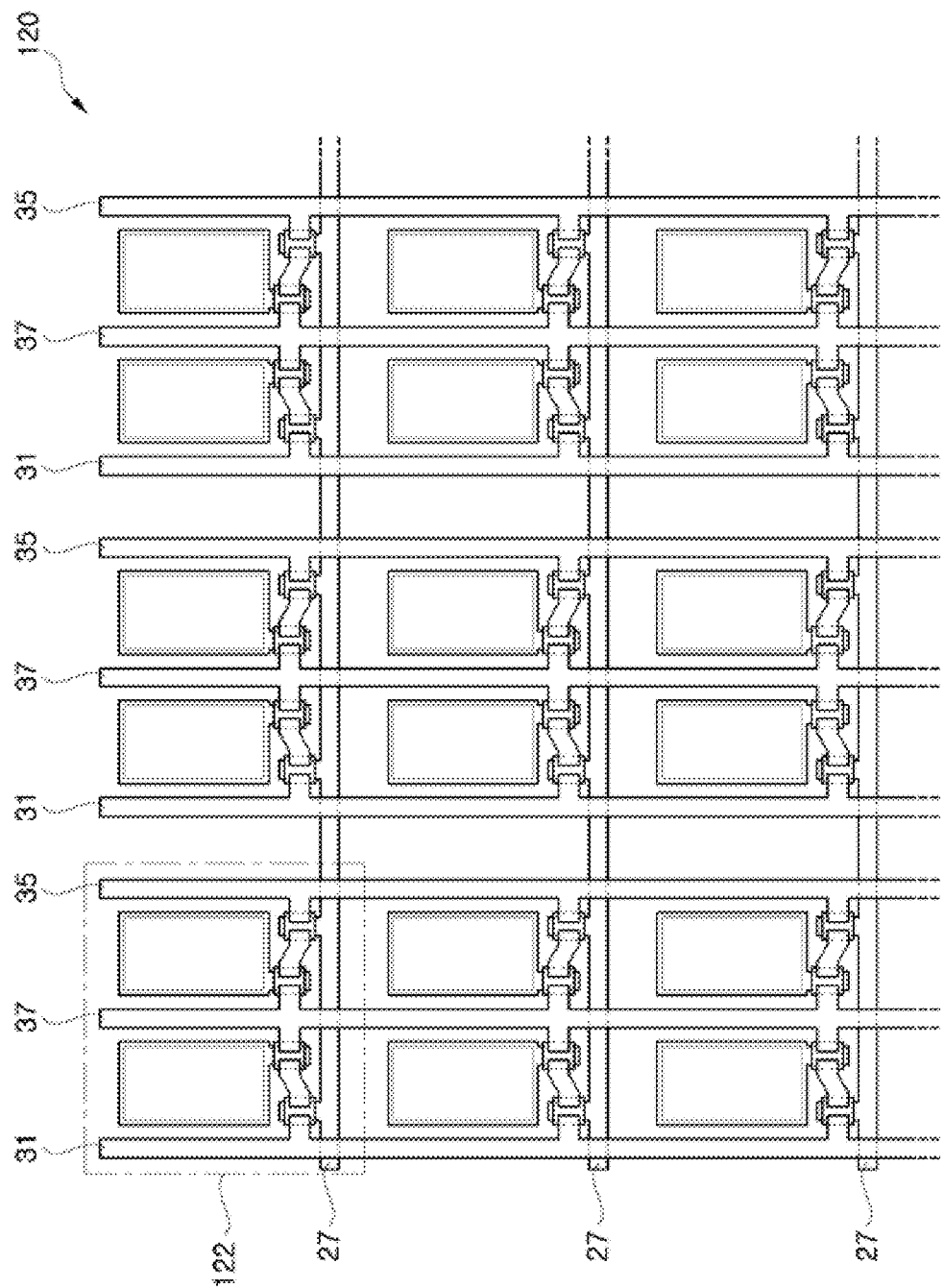
FIG. 4 is a partial plan view of a bio-sensing chip of the biosensor according to the first exemplary embodiment of the present disclosure.

FIG. 4 is a partial plan view of a bio-sensing chip of the biosensor according to the first exemplary embodiment of the present disclosure.

Referring to FIG. 4, the biosensor 100 according to the first exemplary embodiment includes the bio-sensing chip 120, which includes a plurality of sub-cells 122. As shown in the drawing, the sub-cells 122 may be regularly arranged in a matrix, in which a plurality of sub-cells 122 is arranged in a column along gate lines 27 and is arranged in a row along sensing readout lines 31, reference readout lines 35 and Vdd lines 37.

Here, each of the gate lines 27 extends to be electrically connected to the gate driving pad 170. Further, each of the sensing readout lines 31 and the reference readout lines 35 extends to be electrically connected to the readout pad 160 and each of the Vdd lines 37 extends to be electrically connected to the Vdd pad 180.

Figure 5:
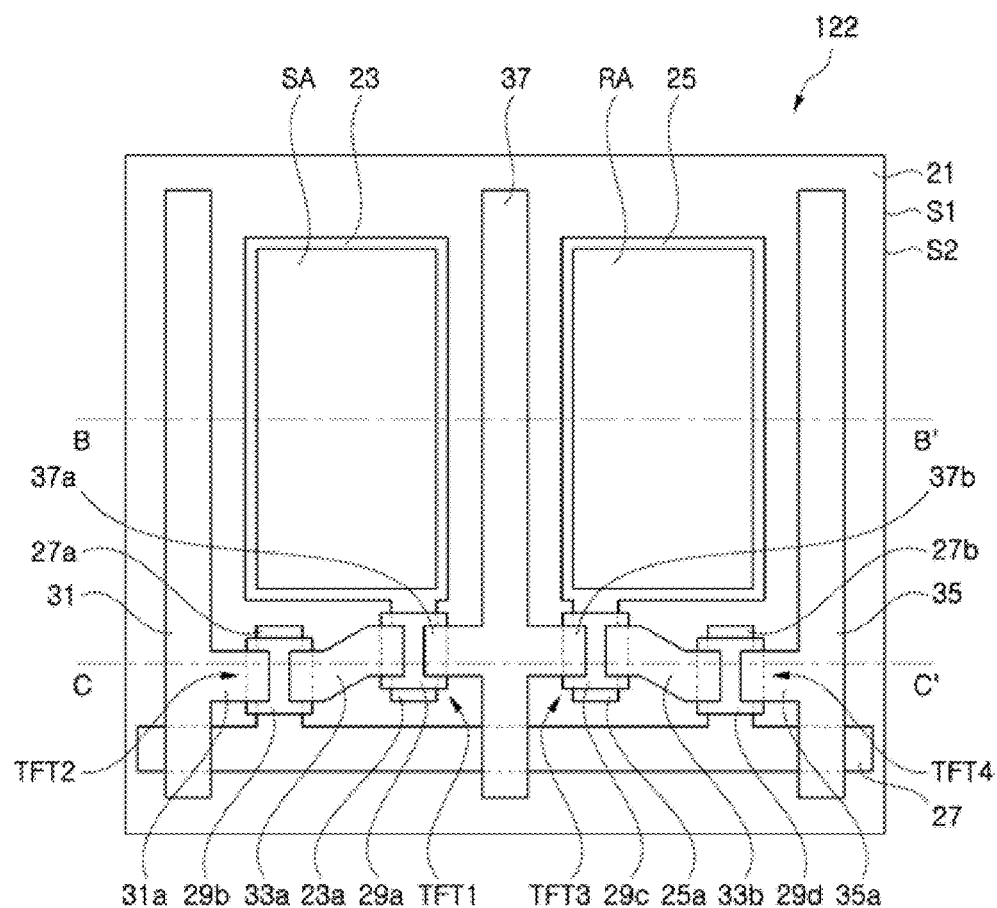
FIG. 5 is a plan view of a sub-cell of the bio-sensing chip according to the first exemplary embodiment of the present disclosure.
Figure 6A:
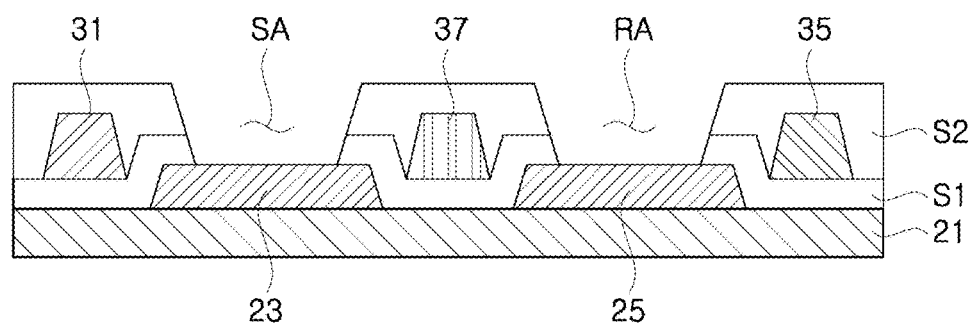
FIG. 6a shows cross-sectional views taken along lines B-B' of FIG. 5.
Figure 6B:
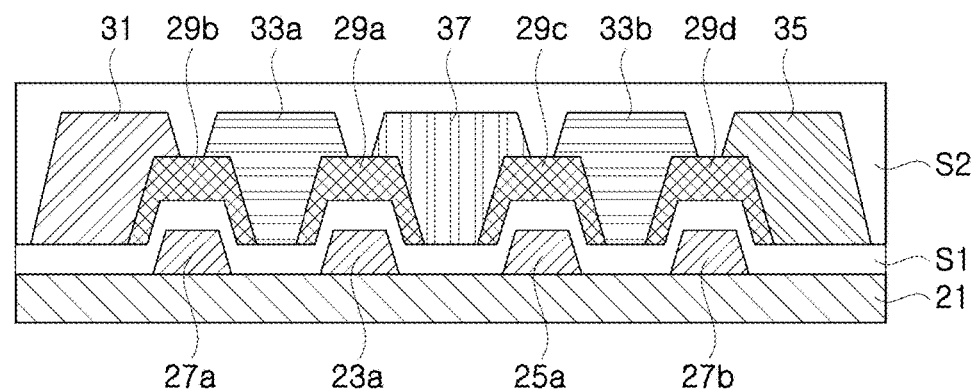
FIG. 6b shows cross-sectional views taken along lines C-C' of FIG. 5.

FIG. 5 is a plan view of a sub-cell of the bio-sensing chip according to the first exemplary embodiment of the present disclosure and FIG. 6a and FIG. 6b shows cross-sectional views taken along lines B-B' and C-C' of FIG. 5, respectively.

As described above, the bio-sensing chip 120 includes a plurality of sub-cells 122, which are electrically connected to each other. The sub-cell 122 will be described in more detail with reference to FIG. 5, FIG. 6a and FIG. 6b.

The sub-cell 122 serves to detect an electrical signal generated by the reaction layer 130 through reaction between the biological sample and the biochemical reaction reagent in the reaction layer 130 and includes an analysis sensing region SA and a reference sensing region RA, as shown in FIG. 4.

The analysis sensing region SA is a region for sensing an electrochemical signal from the biological sample or from the biological sample and the biochemical reaction reagent. The reference sensing region RA is a region for measuring a reference value for correcting the electrochemical signal detected by the analysis sensing region SA. In the biosensor 100 according to this exemplary embodiment, since the analysis sensing region SA senses a signal for analysis, which in turn is corrected with reference to a signal sensed by the reference sensing region RA, it is possible to improve accuracy of a measurement value with respect to a biological sample corresponding to a measurement target substance.

As shown in FIG. 5, each of the analysis sensing region SA and the reference sensing region RA may have a certain area. In addition, as shown in FIG. 6a, each of the analysis sensing region SA and the reference sensing region RA may have a certain depth. Accordingly, each of the analysis sensing region SA and the reference sensing region RA has a large contact area with the reaction layer 130 disposed on the sub-cell 122, thereby enabling more accurate detection of an electrochemical signal output from the reaction layer 130.

The analysis sensing region SA is formed on a first gate surface 23 and the reference sensing region RA is formed on a second gate surface 25. Thus, each of the first gate surface 23 and the second gate surface 25 may have a certain area.

The sub-cell 122 includes four thin film transistors TFT1, TFT2, TFT3, TFT4 for processing signals transferred through the first and second gate surfaces 23, 25.

The first thin film transistor TFT1 senses signals output from the first gate surface 23 corresponding to the analysis sensing region SA. To this end, a first gate electrode 23a of the first thin film transistor TFT1 is electrically connected to the first gate surface 23. In addition, a first source electrode 37a of the first thin film transistor TFT1 is electrically connected to the Vdd line 37, and a drain electrode of the first thin film transistor TFT1 is electrically connected to the second thin film transistor TFT2 through a first connection electrode 33a. The first gate electrode 23a protrudes from the first gate surface 23 and the first source electrode 37a protrudes from the Vdd line 37.

The second thin film transistor TFT2 can read out an electrochemical signal output from the first thin film transistor TFT1. To this end, a source electrode of the second thin film transistor TFT2 is electrically connected to the first thin film transistor TFT1 by the first connection electrode 33a. In addition, a third gate electrode 27a of the second thin film transistor TFT2 is electrically connected to the gate line 27 and a first drain electrode 31a of the second thin film transistor TFT2 is electrically connected to the sensing readout line 31. The third gate electrode 27a protrudes from the gate line 27 and the first drain electrode 31a protrudes from the sensing readout line 31.

The third thin film transistor TFT3 senses a signal output from the second gate surface 25 corresponding to the reference sensing region RA. To this end, a second gate electrode 25a of the third thin film transistor TFT3 is electrically connected to the second gate surface 25. Further, a second source electrode 37b of the third thin film transistor TFT3 is electrically connected to the Vdd line 37, and a drain electrode of the third thin film transistor TFT3 is electrically connected to the fourth thin film transistor TFT4 through a second connection electrode 33b. The second gate electrode 25a protrudes from the second gate surface 25 and the second source electrode 37b protrudes from the Vdd line 37.

The fourth thin film transistor TFT4 can read out a reference electrochemical signal output from the third thin film transistor TFT3. To this end, a source electrode of the fourth thin film transistor TFT4 is electrically connected to the third thin film transistor TFT3 by the second connection electrode 33b. In addition, a fourth gate electrode 27b of the fourth thin film transistor TFT4 is electrically connected to the gate line 27 and a second drain electrode 35a of the fourth thin film transistor TFT4 is electrically connected to the reference readout line 35. The fourth gate electrode 27b protrudes from the gate line 27 and the second drain electrode 35a protrudes from the reference readout line 35.

Referring to FIG. 6a and FIG. 6b, a stack structure of each component of the sub-cell 122 will now be described. First, referring to FIG. 6a, a first gate surface 23 and a second gate surface 25 each having a certain area are disposed on a substrate 21 so as to be separated from each other. In addition, a first insulation layer S1 is disposed over the entirety of the substrate 21 excluding a portion of an upper surface of each of the first gate surface 23 and the second gate surface 25. That is, the upper surface of each of the first gate surface 23 and the second gate surface 25 may be exposed by the first insulation layer S1.

A sensing readout line 31, a Vdd line 37 and a reference readout line 35 are formed on the first insulation layer S1. The sensing readout line 31 is disposed at an edge of the sub-cell 122 outside the first gate surface 23 and the reference readout line 35 is disposed at an edge of the sub-cell 122 outside the second gate surface 25. The Vdd line 37 is disposed between the first gate surface 23 and the second gate surface 25.

Then, a second insulation layer S2 is formed to cover the sensing readout line 31, the reference readout line 35 and the Vdd line 37. The second insulation layer S2 may be formed cover the overall area excluding the first gate surface 23 and the second gate surface 25 with FIG. 6a or without FIG. 14 being exposed by the first insulation layer S1.

As the first insulation layer S1 and the second insulation layer S2 are disposed as above, the upper surface of each of the first gate surface 23 and the second gate surface 25 may have a groove (or well) formed by the first insulation layer S1 and the second insulation layer S2.

Next, referring to FIG. 6b, a stack structure of each of the first to fourth thin film transistors TFT1, TFT2, TFT3, TFT4 will be described. First to fourth gate electrodes 23a, 25a, 27a, 27b are disposed on the substrate 21 so as to be separated from each other. In addition, a first insulation layer S1 is disposed to cover the first to fourth gate electrodes 23a, 25a, 27a, 27b and first to fourth semiconductor active layers 29a, 29b, 29c, 29d are disposed above the first to fourth gate electrodes 23a, 25a, 27a, 27b, respectively.

A sensing readout line 31 is disposed to cover a portion of the second semiconductor active layer 29b and a first connection electrode 33a is disposed between the first semiconductor active layer 29a and the second semiconductor active layer 29b to cover a portion of an upper surface of each of the first semiconductor active layer 29a and the second semiconductor active layer 29b. Further, a Vdd line 37 is disposed between the first semiconductor active layer 29a and the third semiconductor active layer 29c to cover a portion of an upper surface of each of the first semiconductor active layer 29a and the third semiconductor active layer 29c. Further, a second connection electrode 33b is disposed between the third semiconductor active layer 29c and the fourth semiconductor active layer 29d to cover a portion of an upper surface of each of the third semiconductor active layer 29c and the fourth semiconductor active layer 29d. Further, a reference readout line 35 is disposed to cover a portion of the fourth semiconductor active layer 29d.

Here, the sensing readout line 31, the first connection electrode 33a, the Vdd line 37, the second connection electrode 33b and the reference readout line 35 are separated from each other. Although not shown in the drawings, a portion of the sensing readout line 31 covering the second semiconductor active layer 29b is the first drain electrode 31a and a portion of the Vdd line 37 covering the first semiconductor active layer 29a is the first source electrode 37a. In addition, a portion of the Vdd line 37 covering the third semiconductor active layer 29c is the second source electrode 37b and a portion of the reference readout line 35 covering the fourth semiconductor active layer 29d is the second drain electrode 35a.

Further, a second insulation layer S2 is disposed to cover the sensing readout line 31, the first connection electrode 33a, the Vdd line 37, the second connection electrode 33b and the reference readout line 35. By the second insulation layer S2, the sensing readout line 31, the first connection electrode 33a, the Vdd line 37, the second connection electrode 33b and the reference readout line 35 can be electrically insulated from one another.

FIG. 7 to FIG. 10 are plan views illustrating a method of fabricating a sub-cell according to the first exemplary embodiment of the present disclosure.

The following description will be given of a method of fabricating the sub-cell 122 according to the first exemplary embodiment of the present disclosure.

Figure 7:
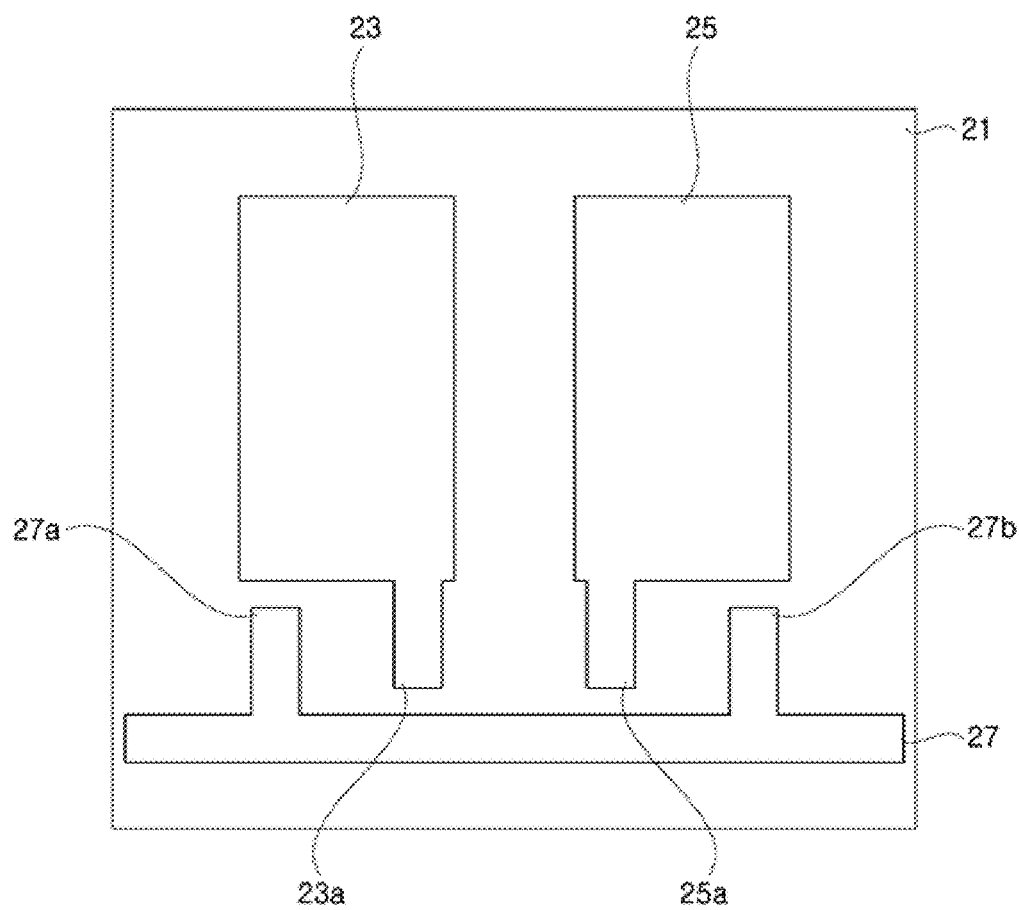
FIG. 7 to FIG. 10 are plan views illustrating a method of fabricating a sub-cell according to the first exemplary embodiment of the present disclosure.

First, referring to FIG. 7, a first gate surface 23, a second gate surface 25 and a gate line 27 are formed on a substrate 21. Here, a portion of the first gate surface 23 may protrude towards the gate line 27 to form a first gate electrode 23a and a portion of the second gate surface 25 may protrude towards the gate line 27 to form a second gate electrode 25a. Further, a portion of the gate line 27 may protrude towards the first gate surface 23 to form a third gate electrode 27a and a portion of the gate line 27 may protrude towards the second gate surface 25 to form a fourth gate electrode 27b. The first gate surface 23, the second gate surface 25 and the gate line 27 may be separated from each other to be electrically insulated from one another on the substrate 21.

As described above, the first and second gate surfaces 23, 25, the gate line 27 and the first to fourth gate electrodes 23a, 25a, 27a, 27b may be formed by depositing a gate electrode material on an overall upper surface of the substrate 21, followed by patterning.

Figure 8:
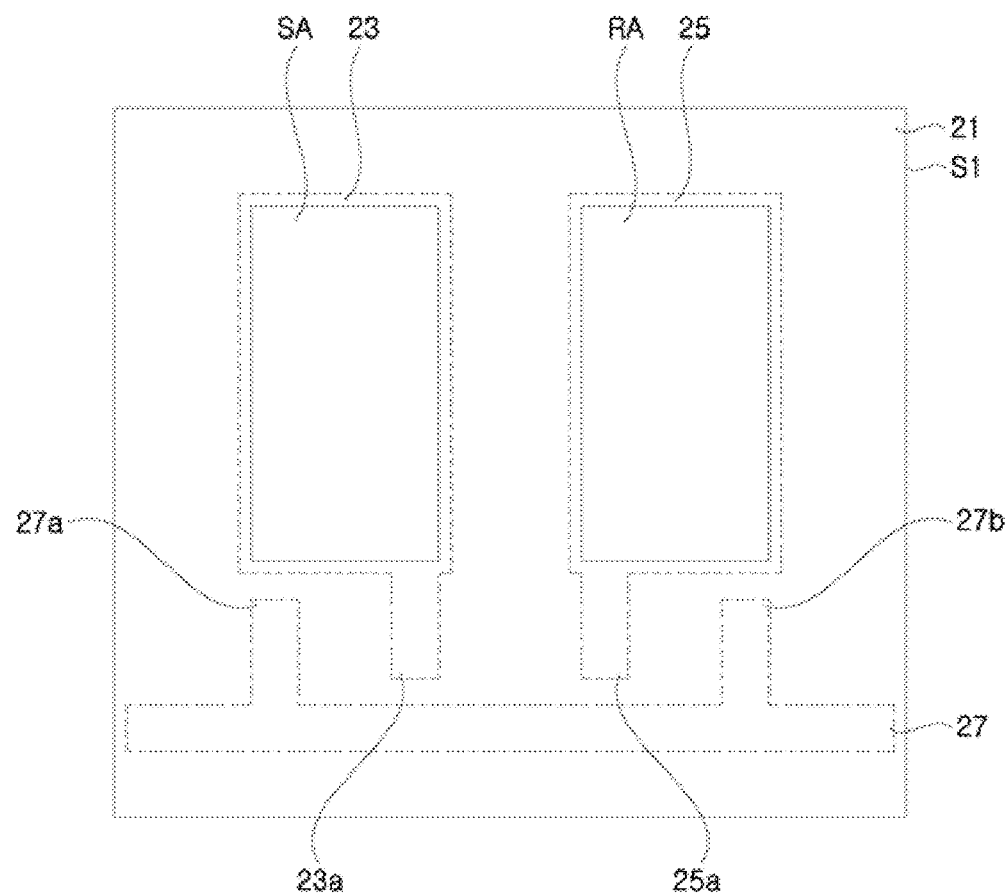

Then, referring to FIG. 8, a first insulation layer S1 is formed on the substrate 21 to cover the first to fourth gate electrodes 23a, 25a, 27a, 27b and the gate line 27. Here, the first insulation layer S1 may be formed to cover a portion of each of the first gate surface 23 and the second gate surface 25 such that an upper surface of each of the first gate surface 23 and the second gate surface 25 is exposed or not exposed. As a result, an analysis sensing region SA and a reference sensing region RA may be formed on the first gate surface 23 and the second gate surface 25, respectively.

Figure 9:
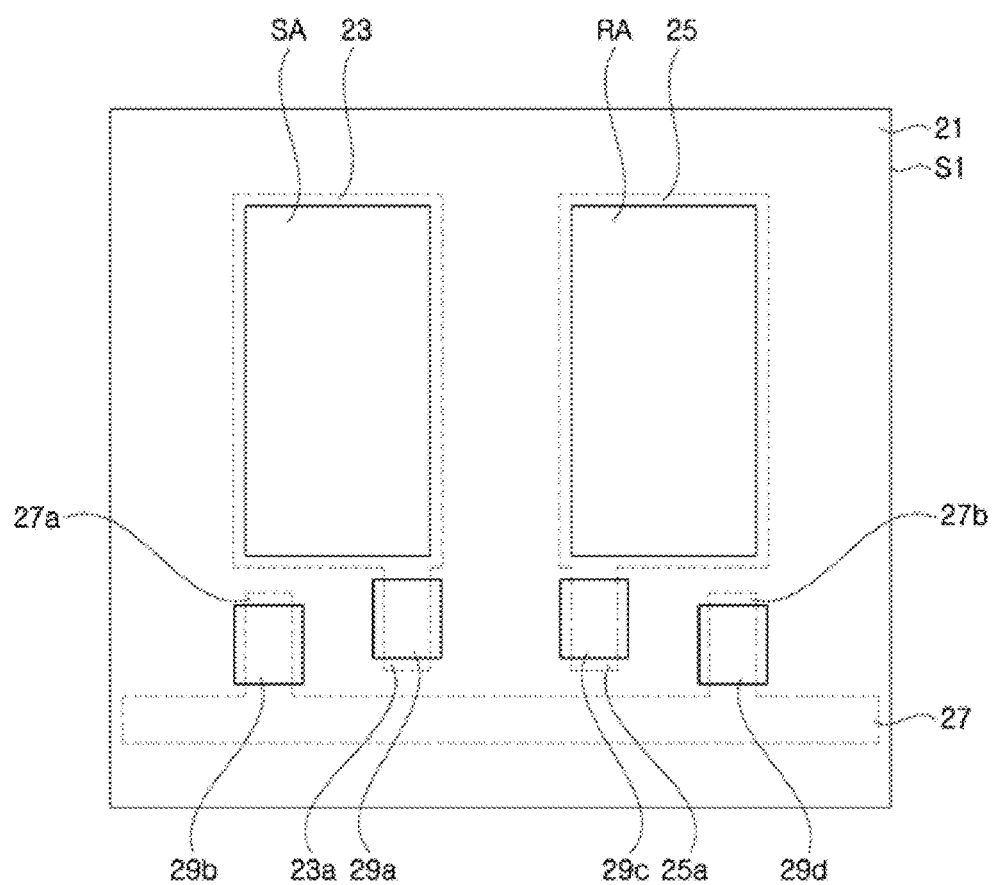

Then, referring to FIG. 9, first to fourth semiconductor active layers 29a, 29b, 29c, 29d may be formed on the first to fourth gate electrodes 23a, 25a, 27a, 27b, respectively. Each of the first to fourth semiconductor active layers 29a, 29b, 29c, 29d may be formed in a shape covering a portion of each of the first to fourth gate electrodes 23a, 25a, 27a, 27b. In this exemplary embodiment, each of the first to fourth semiconductor active layers 29a, 29b, 29c, 29d may be formed of at least one of amorphous silicon, crystalline silicon, and an oxide semiconductor. The oxide semiconductor may include at least one of In, Ga and Zn oxides.

The first to fourth semiconductor active layers 29a, 29b, 29c, 29d may be formed by depositing a material for a semiconductor active layer on the first insulation layer S1, followed by patterning.

Figure 10:
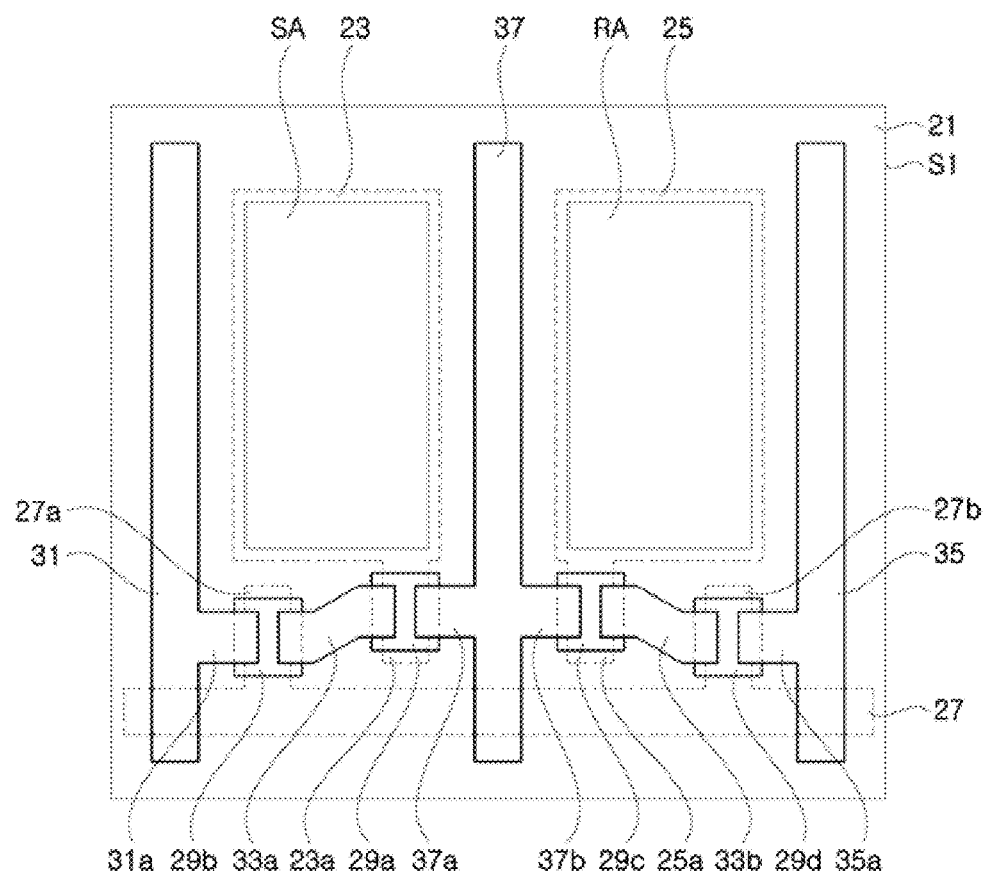

Referring to FIG. 10, a sensing readout line 31 is formed outside the first gate surface 23, a Vdd line 37 is formed between the first gate surface 23 and the second gate surface 25, and a reference readout line 35 is formed outside the second gate surface 25. In addition, a first connection electrode 33a is formed between the first semiconductor active layer 29a and the second semiconductor active layer 29b such that the first semiconductor active layer 29a and the second semiconductor active layer 29b are electrically connected to each other therethrough. Further, a second connection electrode 33b is formed between the third semiconductor active layer 29c and the fourth semiconductor active layer 29d such that the third semiconductor active layer 29c and the fourth semiconductor active layer 29d are electrically connected to each other therethrough.

Further, a first drain electrode 31a protruding from the sensing readout line 31 may be formed to cover a portion of the second semiconductor active layer 29b, and a second drain electrode 35a protruding from the reference readout line 35 may be formed to cover a portion of the fourth semiconductor active layer 29d. Further, a first source electrode 37a protruding from the Vdd line 37 may be formed to cover a portion of the first semiconductor active layer 29a, and a second source electrode 37b protruding from the Vdd line 37 may be formed to cover a portion of the third semiconductor active layer 29c.

In this exemplary embodiment, each of the first gate surface 23, the second gate surface 25, the gate line 27, the sensing readout line 31, the reference readout line 35 and the Vdd line 37 may have a monolayer structure or a stack structure formed of at least one of Pt, Au, Ag, al, Al—Nd, Al—Cu, Mo, Ti, Ta and Cr. Alternatively, each of the first gate surface 23, the second gate surface 25, the gate line 27, the sensing readout line 31, the reference readout line 35 and the Vdd line 37 may have a monolayer structure or a stack structure formed of at least one of InSnO, SnO, InZnO and ZnO.

Then, a second insulation layer S2 is formed on the overall upper surface of the substrate excluding the analysis sensing region SA and the reference sensing region RA, thereby forming a sub-cell 122 as shown in FIG. 5.

Figure 11:
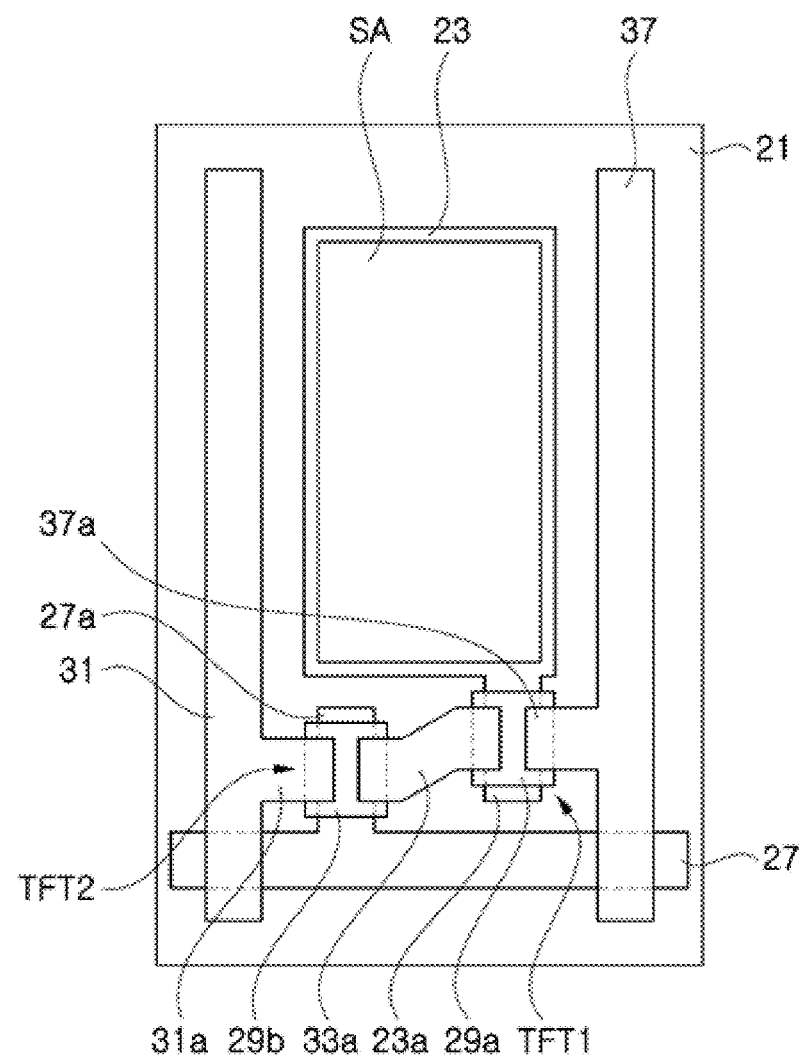
FIG. 11 is a plan view of a sub-cell according to a second exemplary embodiment of the present disclosure.

FIG. 11 is a plan view of a sub-cell according to a second exemplary embodiment of the present disclosure.

Referring to FIG. 11, the sub-cell 122 according to the second exemplary embodiment has an analysis sensing region SA, and includes a first gate surface 23, a gate line 27, a first semiconductor active layer 29a, a second semiconductor active layer 29b, a sensing readout line 31 and a Vdd line 37. In description of the second exemplary embodiment, descriptions of the same components as those of the first exemplary embodiment will be omitted.

As compared with the sub-cell according to the first exemplary embodiment, the sub-cell 122 according to the second exemplary embodiment does not include the reference sensing region RA. Accordingly, an electrochemical signal output from the reaction layer 130 contacting the sub-cell 122 is sensed by the first thin film transistor TFT1 through the analysis sensing region SA and is then read out through the second thin film transistor TFT2.

Connection between the gate electrode, the source electrode and the drain electrode of the first thin film transistor TFT1 and the second thin film transistor TFT2 is the same as in the sub-cell according to the first exemplary embodiment. In the second exemplary embodiment, only the first source electrode 37a protrudes from the Vdd line 37 and is electrically connected to the first thin film transistor TFT1, unlike in the exemplary embodiment.

That is, the first gate electrode 23a of the first thin film transistor TFT1 is electrically connected to the first gate surface 23, on which the analysis sensing region SA is formed, so as to contact the biological sample or the biological sample and the biochemical reaction reagent.

Figure 12:
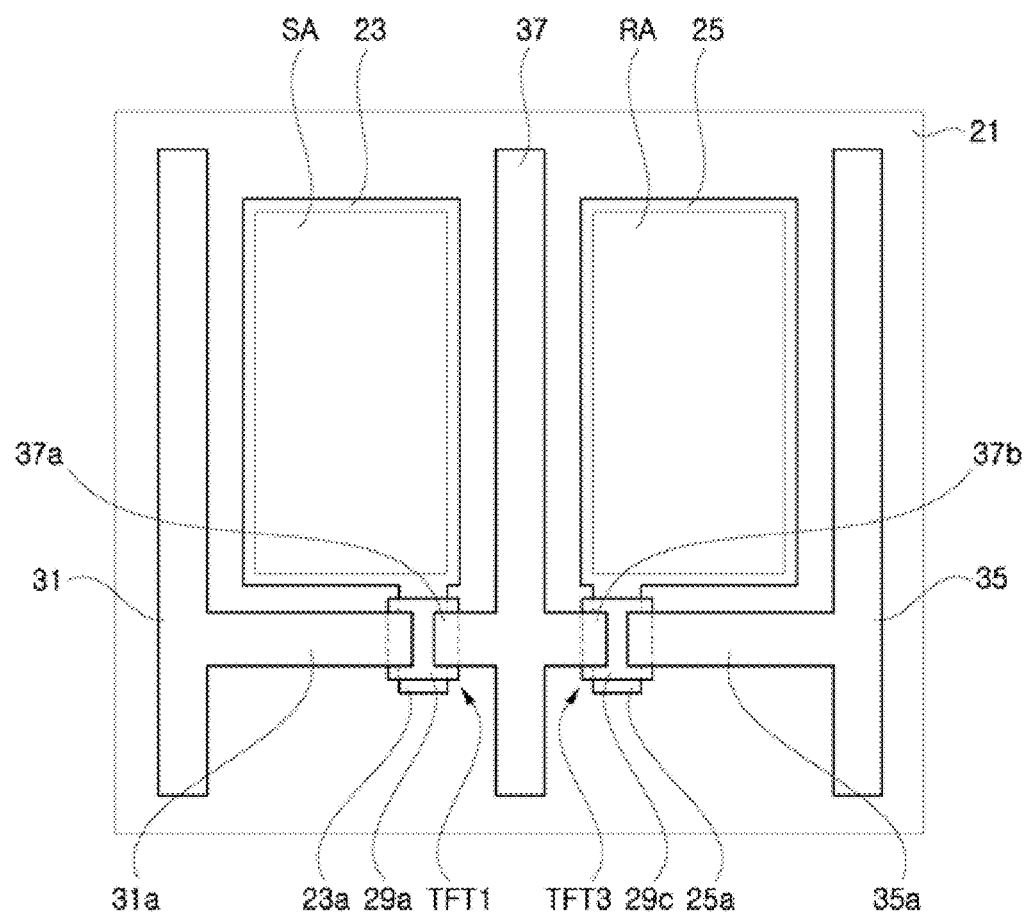
FIG. 12 is a plan view of a sub-cell according to a third exemplary embodiment of the present disclosure.

FIG. 12 is a plan view of a sub-cell according to a third exemplary embodiment of the present disclosure.

Referring to FIG. 12, the sub-cell 122 according to the third exemplary embodiment includes an analysis sensing region SA and a reference sensing region RA. In description of the third exemplary embodiment, descriptions of the same components as those of the first exemplary embodiment will be omitted.

As compared with the sub-cell according to the first exemplary embodiment, the sub-cell 122 according to the third exemplary embodiment does not include the second thin film transistor TFT2 and the fourth thin film transistor TFT4. Thus, a signal output from the reaction layer 130 through the analysis sensing region SA is sensed by the first thin film transistor TFT1 and is then output through the sensing readout line 31.

Further, a signal output from the reaction layer 130 through the reference sensing region RA is sensed by the third thin film transistor TFT3 and is then output through the reference readout line 35.

According to this exemplary embodiment, the structures of the first gate electrode 23a and the first source electrode 37a of the first thin film transistor TFT1 are the same as those of the first exemplary embodiment, and the first drain electrode 31a protrudes from the sensing readout line 31 and is electrically connected to the first thin film transistor TFT1. In addition, the structures of the second gate electrode 25a and the second source electrode 37b of the third thin film transistor TFT3 are the same as those of the first exemplary embodiment, and the second drain electrode 35a protrudes from the reference readout line 35 and is electrically connected to the third thin film transistor TFT3.

Figure 13:
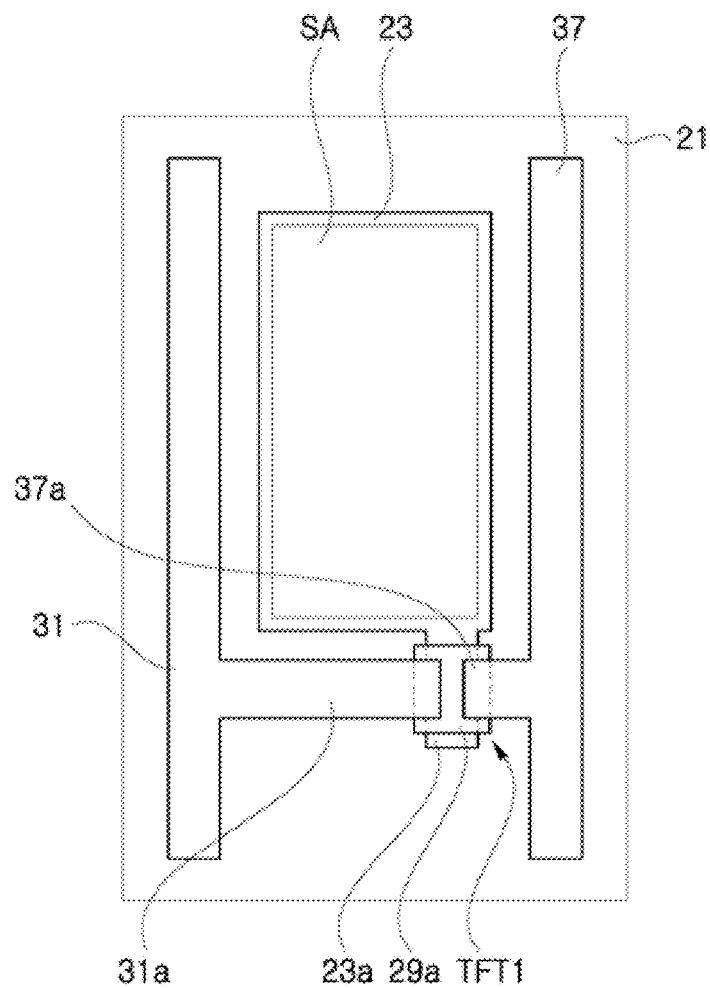
FIG. 13 is a plan view of a sub-cell according to a fourth exemplary embodiment of the present disclosure.

FIG. 13 is a plan view of a sub-cell according to a fourth exemplary embodiment of the present disclosure.

Referring to FIG. 13, the sub-cell 122 according to the fourth exemplary embodiment has an analysis sensing region SA, and includes a first gate surface 23, a gate line 27, a first semiconductor active layer 29a, a sensing readout line 31 and a Vdd line 37. In description of the fourth exemplary embodiment, descriptions of the same components as those of the first and third exemplary embodiments will be omitted.

As compared with the sub-cell according to the third exemplary embodiment, the sub-cell 122 according to the fourth exemplary embodiment does not include the reference sensing region RA of the sub-cell according to the third exemplary embodiment. Accordingly, an electrochemical signal output from the reaction layer 130 contacting the sub-cell 122 is sensed by the first thin film transistor TFT1 through the analysis sensing region SA and is then readout through the sensing readout line 31.

Figure 14:
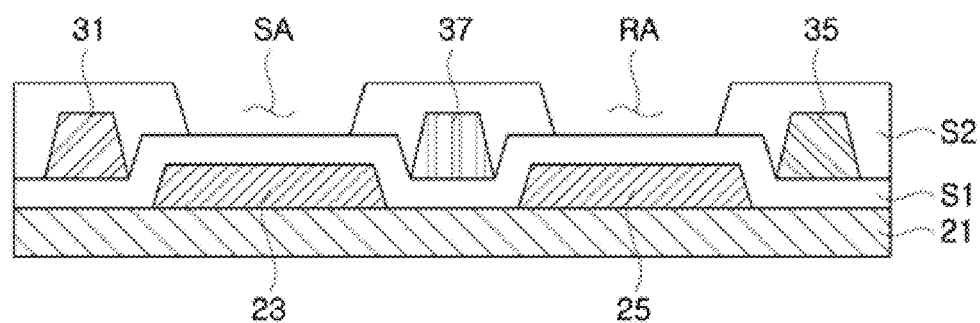
FIG. 14 is a cross-sectional view taken along lines B-B' showing another exemplary embodiment of FIG. 6a showing that the first gate surface 23 and the second gate surface 25 not being exposed to reaction layer 130 through the first insulation layer S1.

FIG. 14 is a cross-sectional view taken along lines B-B' in FIG. 5 showing another exemplary embodiment of FIG. 6a showing that the first gate surface 23 and the second gate surface 25 not being exposed to reaction layer 130 through the first insulation layer S1.

Referring to FIG. 14, the sub-cell 122 according to the fifth exemplary embodiment includes an analysis sensing region SA and a reference sensing region RA. As compared with the sub-cell shown in FIG. 6a, the sub-cell 122 according to the fifth exemplary embodiment is generally similar to the sub-cell according to the first exemplary embodiment except that the first insulation layer S1 is disposed on the first and second gate surfaces 23, 25, as shown in FIG. 14. In description of the third exemplary embodiment, descriptions of the same components as those of the first exemplary embodiment will be omitted.

Thus, the reaction layer 130 disposed on the bio-sensing chip 120 may contact the first insulation layer S1 disposed on the first and second gate surfaces 23, 25. Each of the first and second gate surfaces 23, 25 is electrically connected to the first and second gate electrodes 23a, 25a, respectively. When electric signal is applied to the first and second gate electrodes 23a, 25a, polarity is generated on the first insulation layer S1, thereby causing polar coupling between the first insulation layer S1 and the reaction layer 130.

As polarity is generated on a contact surface between the first insulation layer S1 and the first and second gate electrodes 23a, 25a to which electric signal is applied, polarity can be generated on a contact surface between the reaction layer 130 and the first insulation layer S1 corresponding to a rear surface of the contact surface between the first insulation layer S1 and the first and second gate electrodes 23a, 25a. As a result, polar coupling between the first insulation layer S1 and the reaction layer 130 can occur.

As such, when polar coupling between the first insulation layer S1 and the reaction layer 130 occurs, a potential difference occurs between the reaction layer 130 and the upper electrode 150 disposed thereon. The potential difference can be output to the sensing readout line 31 and the reference readout line 35 through the first and second drain electrodes 31a, 35a.

As described above, even in the structure wherein the first insulation layer S1 is disposed on the first and second gate surfaces 23, 25, electrical signals output from the reaction layer 130 can be sensed by the first and second thin film transistors TFT1, TFT2. Furthermore, since the reaction layer 130 does not directly contact the first and second gate surfaces 23, 25, the biosensor can examine a bio sample which is likely to be damaged due to electrical contact with the reaction layer 130. The bio sample is likely to be damaged due to electrical contact before electrical contact, and may be, for example, an electrolyte type bio sample.

As such, according to the exemplary embodiments, the biosensor can measure voltage-current characteristics in a linear region and a saturation region through examination with respect to a target substance using thin film transistors. In addition, the biosensor according to the exemplary embodiments can obtain various output data depending upon gate voltage and source voltage of the thin film transistors, and can obtain not only gate voltage-drain current values but also drain voltage-drain current values, thereby enabling accurate analysis of a target substance through analysis with respect to various voltage and current characteristics.

Furthermore, in the biosensor according to the exemplary embodiments, each of the sub-cells includes an analysis sensing region for measurement of voltage and current characteristics using an actual target substance, and a reference sensing region for correction and measurement of a reference value such that accurate analysis can be achieved through correction of a measurement value measured by the analysis sensing region based on the reference value measured by the reference sensing region.

Although some exemplary embodiments have been described herein, it should be understood by those skilled in the art that these embodiments are given by way of illustration only, and that various modifications, variations, and alterations can be made without departing from the spirit and scope of the present disclosure. Therefore, the scope of the present disclosure should be limited only by the accompanying claims and equivalents thereof.

<Description of Reference Numeral>

| | |
|---|---|
| 100: biosensor | |
| 110: mount | |
| 120: bio-sensing chip | |
| 122: sub-cell | |
| 21: substrate | 23: first gate surface |
| 23a: first gate electrode | 25: second gate surface |
| 25a: second gate electrode | 27: gate line |
| 27a: third gate electrode | 27b: fourth gate electrode |
| 29a: first semiconductor active layer | 29b: second semiconductor active layer |
| 29c: third semiconductor active layer | 29d: fourth semiconductor active layer |
| 31: sensing readout line | 31a: first drain electrode |
| 33a: first connection electrode | 33b: second connection electrode |
| 35: reference readout line | 35a: second drain electrode |
| 37: Vdd line | 37a: first source electrode |
| 37b: second source electrode | |
| 130: reaction layer | 140: wall |
| 150: upper electrode | 160: readout pad |
| 170: gate driving pad | 180: Vdd pad |
| SA: analysis sensing region | RA: reference sensing region |
| S1: first insulation layer | S2: second insulation layer |

TFT1~TFT4: first to fourth thin film transistors

What is claimed is:

1. A biosensor comprising:
a mount;
a bio-sensing chip disposed on the mount and comprising at least one thin film transistor;
a reaction layer disposed on the bio-sensing chip and comprising at least one of a biological sample and a biochemical reaction reagent;
an upper electrode disposed on the reaction layer and supplying electric signal to the reaction layer; and
at least one pad disposed on the bio-sensing chip and electrically connected to the bio-sensing chip,
wherein the bio-sensing chip comprises a plurality of sub-cells regularly arranged and electrically connected to each other.

2. The biosensor according to claim 1, wherein each of the sub-cells comprises a first thin film transistor contacting the reaction layer and detecting at least one of the biological sample and the biochemical reaction reagent on the reaction layer.

3. The biosensor according to claim 2, wherein each of the sub-cells comprises a second thin film transistor electrically connected to the first thin film transistor and reading out an electrochemical signal output from the first thin film transistor.

4. The biosensor according to claim 3, wherein each of the sub-cells comprises a third thin film transistor contacting the reaction layer and detecting at least one of the biological sample and the biochemical reaction reagent on the reaction layer.

5. The biosensor according to claim 4, wherein each of the sub-cells comprises a fourth thin film transistor electrically connected to the third thin film transistor and reading out an electrochemical signal output from the third thin film transistor.

6. The biosensor according to claim 2, further comprising:
a sensing readout line and a Vdd line,
wherein a gate electrode of the first thin film transistor contacts the reaction layer, a source electrode of the first thin film transistor is electrically connected to the Vdd line, and a drain electrode of the first thin film transistor is electrically connected to the sensing readout line.

7. The biosensor according to claim 3, further comprising:
a sensing readout line, a Vdd line, and a gate line,
wherein a gate electrode of the first thin film transistor contacts the reaction layer, a source electrode of the first thin film transistor is electrically connected to the Vdd line, a drain electrode of the first thin film transistor is electrically connected to a source electrode of the second thin film transistor, a drain electrode of the second thin film transistor is electrically connected to the sensing readout line, and a gate electrode of the second thin film transistor is electrically connected to the gate line.

8. The biosensor according to claim 4, further comprising:
a sensing readout line, a reference readout line, and a Vdd line,
wherein a gate electrode of the first thin film transistor contacts the reaction layer, a source electrode of the first thin film transistor is electrically connected to the Vdd line, a drain electrode of the first thin film transistor is electrically connected to the sensing readout line, a gate electrode of the third thin film transistor is electrically connected to the reaction layer, a source electrode of third thin film transistor is electrically connected to the Vdd line, and a drain electrode of the third thin film transistor is electrically connected to the reference readout line.

9. The biosensor according to claim 5, further comprising:
a sensing readout line, a reference readout line, a Vdd line, and a gate line,
wherein a gate electrode of the third thin film transistor contacts the reaction layer, a source electrode of third thin film transistor is electrically connected to the Vdd line, a drain electrode of the third thin film transistor is electrically connected to a source electrode of the fourth thin film transistor, a drain electrode of the fourth thin film transistor is electrically connected to the reference readout line, and a gate electrode of the fourth thin film transistor is electrically connected to the gate line.

10. The biosensor according to claim 1, wherein each of the sub-cells comprises:
a gate surface disposed on the mount and provided at one side thereof with a first gate electrode;
a first semiconductor active layer disposed on the first gate electrode;
a first drain electrode disposed on the first semiconductor active layer and electrically connected to the first semiconductor active layer; and
a first source electrode disposed on the first semiconductor active layer and electrically connected to the first semiconductor active layer while being electrically insulated from the first drain electrode.

11. The biosensor according to claim 10, wherein the gate surface contacts the reaction layer.

12. The biosensor according to claim 10, wherein one of the at least one pad is a readout pad, and the first drain electrode is electrically connected to the readout pad.

13. The biosensor according to claim 10, wherein one of the at least one pad is a Vdd pad, and the first source electrode is electrically connected to the Vdd pad.

14. The biosensor according to claim 10, further comprising:
a gate line disposed on the mount and comprising a second gate electrode; and
a second semiconductor active layer disposed on the second gate electrode.

15. The biosensor according to claim 14, wherein the first drain electrode is electrically connected at one side thereof to the first semiconductor active layer and at the other side thereof to the second semiconductor active layer.

16. The biosensor according to claim 10, wherein each of the sub-cells comprises:
an analysis sensing region and a reference sensing region, each of the analysis sensing region and the reference sensing region comprising a gate surface, a first semiconductor active layer, a first drain electrode, and a first source electrode.

17. The biosensor according to claim 16, wherein the analysis sensing region senses an electrochemical signal output from the reaction layer, and the reference sensing region measures a reference value for correcting the electrochemical signal sensed by the analysis sensing region.

* * * * *